United States Patent [19]

Kedem et al.

[11] Patent Number: 5,213,110
[45] Date of Patent: May 25, 1993

[54] PISTOL-GRIP VACUUM SOFT TISSUE BIOPSY DEVICE

[75] Inventors: Uzi Kedem, Moshav Gan Haim; Mordechai Rubinstein, Rishon Le-Zion, both of Israel

[73] Assignee: Du-Kedem Projects Ltd., Moshav Gan Haim, Israel

[21] Appl. No.: 851,790

[22] Filed: Mar. 16, 1992

[51] Int. Cl.$^5$ .............................................. A61B 10/00
[52] U.S. Cl. ...................................................... 128/754
[58] Field of Search .................... 128/749, 751–754; 606/167, 170

[56] References Cited

U.S. PATENT DOCUMENTS

| 3,561,429 | 2/1971 | Jewett | 128/752 |
| 4,667,684 | 5/1987 | Leigh | 128/754 |
| 4,733,671 | 3/1988 | Mehl | 128/754 |
| 5,048,538 | 9/1991 | Terwilliger et al. | 128/754 |

*Primary Examiner*—Max Hindenberg
*Attorney, Agent, or Firm*—Edward Langer

[57] ABSTRACT

A soft tissue biopsy device provided with a piston retraction mechanism designed as a pistol-grip handle for developing a suction chamber within a housing as the piston slides therein. The suction reaches the cannula tip as it is withdrawn, drawing tissue into a depression on an exposed stylet. When the piston retraction mechanism reaches a preset cam limit point, it automatically releases the piston, which is shot forward and restored to its position in the housing by vacuum-spring action. Thus, the cannula slides quickly over the stylet, cutting the tissue and retaining it in the depression. The entire procedure is performed by a single-handed operation. The inventive biopsy device is designed with a piston and housing which are relatively large in comparison to the cannula diameter. Thus, with initial retraction of the piston, a relatively large suction is developed in the cannula, drawing tissue therein and firmly seating it in the stylet depression.

20 Claims, 3 Drawing Sheets

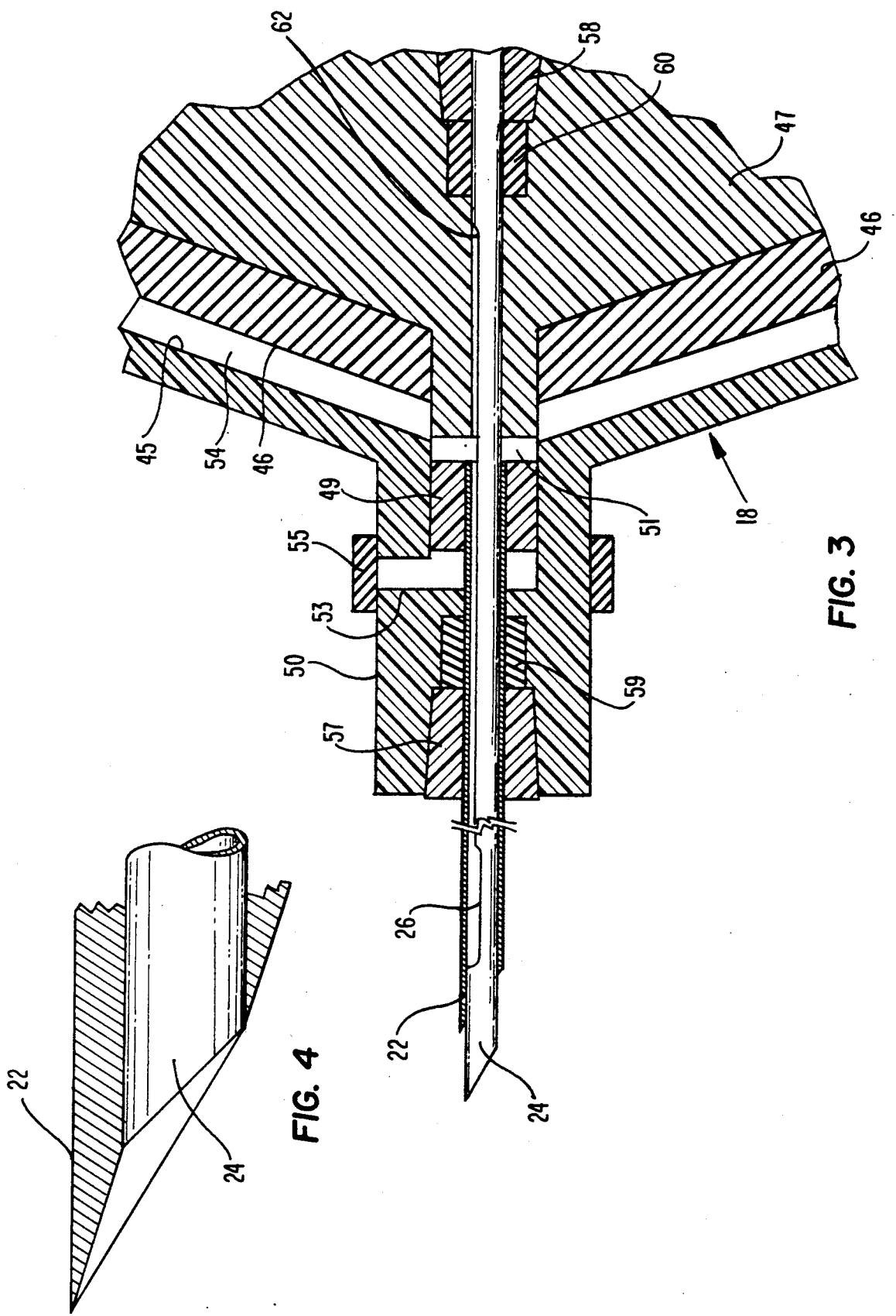

PISTOL-GRIP VACUUM SOFT TISSUE BIOPSY DEVICE

FIELD OF THE INVENTION

The present invention relates to medical instruments and devices for carrying out soft tissue biopsy and aspiration procedures, and more particularly, to a novel soft tissue biopsy device with a pistol-grip handle for single-handed operation.

BACKGROUND OF THE INVENTION

There are known soft tissue biopsy instruments and devices designed as syringes comprising an outer cylindrical body having a piston slidably engaged therein, so as to define a suction chamber. A biopsy cannula extends from one end of the cylindrical body, and a stylet connected to the piston is movable within the biopsy cannula. Such a design is described in European Patent 0 173 653 to Zambelli, and is based on the Menghini needle.

When the stylet point projects from the cannula, it can be inserted through the skin into internal tissue, and suction is then developed by retracting the piston, pulling the stylet into the cannula. By a quick forward motion, the cannula cuts into the tissue, and a tissue fragment is retained therein by the vacuum. When the cannula is removed from under the skin, the vacuum is released by reinserting the piston in the cylinder, and the tissue fragment is dislodged and made available for lab analysis.

A problem with this and other existing biopsy devices is that the vacuum created by the piston is not sufficiently strong to insure retention of the tissue fragment. Thus, as the tissue is removed from the skin, there is a tendency for a portion of the tissue fragment to remain in place, and the amount of tissue available for testing is thereby reduced. These devices require the use of both hands for their operation.

Another method for biopsy procedures is described in U.S. Pat. No. 3,477,423, and features a product sold under the tradename "Tru-Cut", which is commercially available from Travenol Laboratories. In this design the stylet has a depression formed in its distal end, and this depression becomes filled with tissue when the stylet penetrates it. The cannula is slid over the stylet, cutting the tissue portion lodged in the depression, so that a larger quantity of tissue is then available for tests.

A drawback to the "Tru-Cut" design is that it is difficult to use with a very thin needle (gauge higher than 20), since the stylet is thin and not sufficiently rigid to penetrate the tissue, so it may bend or break, with risk of patient injury.

In addition, fine needle aspiration procedures are difficult, owing to the density of tissue which cannot easily be drawn into the small cannula diameter.

Existing tissue biopsy devices are of the single-use, disposable type, and rely on simple designs to achieve low manufacturing costs. As a design criteria, this tends to limit the use of mechanisms which can simplify the procedure.

Therefore, it would be desirable to provide a soft tissue biopsy device which can be adapted for use with high gauge needles, for obtaining required biopsy tissue quantities.

It would also be desirable to provide an easy-to-use tissue biopsy device capable of single-handed operation.

SUMMARY OF THE INVENTION

Accordingly, it is a principal object of the present invention to overcome the above-mentioned disadvantages of prior art devices and provide a soft tissue biopsy device capable of single-handed operation, providing fluid and tissue suction and vacuum-spring action.

In accordance with a preferred embodiment of the present invention, there is provided a soft tissue biopsy device comprising:

a cylindrical housing having a piston slidably seated for retraction therein, the piston having a cannula extending therefrom with a stylet slidably engaged therein along its length;

means for retracting the piston within the housing, to withdraw the cannula and expose the stylet, while developing a suction chamber within the housing and said cannula length; and a cam for limiting retraction of the piston by releasing the piston retraction means, to restore the piston to its position within the housing by vacuum-spring action, such that when the device is inserted into organ tissue to perform a biopsy procedure, retraction of the piston develops the suction chamber and draws a portion of the tissue into a depression formed on a distal end of the stylet, whereupon the cam releases said piston which is shot forward in the housing, and the cannula slides over the stylet to cut and retain the tissue portion in the depression.

In the preferred embodiment, the inventive soft tissue biopsy device is provided with a piston retraction mechanism designed as a pistol-grip handle for single-handed operation. The pistol-grip handle operates the piston retraction mechanism, developing a suction chamber within the housing as the piston slides therein. The suction reaches the cannula tip as it is withdrawn, drawing tissue into a depression on the exposed stylet.

When the piston retraction mechanism reaches a preset cam limit point, it automatically releases the piston, which is shot forward and restored to its position in the housing by vacuum-spring action. Thus, the cannula slides quickly over the stylet, cutting the tissue and retaining it in the depression. The entire procedure is performed by a single-handed operation.

The inventive biopsy device is designed with a piston and housing which are relatively large in comparison to the cannula diameter. Thus, with initial retraction of the piston, a relatively large suction is developed in the cannula, drawing tissue therein and firmly seating it in the stylet depression.

Use of vacuum-spring action for restoration of the piston to its position insures that organ tissue is cut quickly, and the procedure thus minimizes damage and patient discomfort.

The retraction mechanism can limit point is adjustable, allowing for adjustment of the stylet exposure and suction volume.

The cannula and stylet are provided with the piston and cylindrical housing as a disposable syringe unit. Thus, pistol-grip handle can be re-used with an easily replaced syringe unit, for repetition of the biopsy procedure in sanitary fashion. The overall design allows lower production costs to be achieved.

Other features and advantages of the invention will become apparent from the drawings and the description hereinbelow.

BRIEF DESCRIPTION OF THE DRAWINGS

For a better understanding of the invention with regard to the embodiments thereof, reference is made to the accompanying drawings, in which like numerals designate corresponding elements or sections throughout, and in which:

FIG. 3 is a partial detail view of the section of the biopsy device shown in FIG. 2, adding a valve release feature; and FIG. 4 is a detail view of the stylet and cannula tip.

DETAILED DESCRIPTION OF A PREFERRED EMBODIMENT

Figure 1:
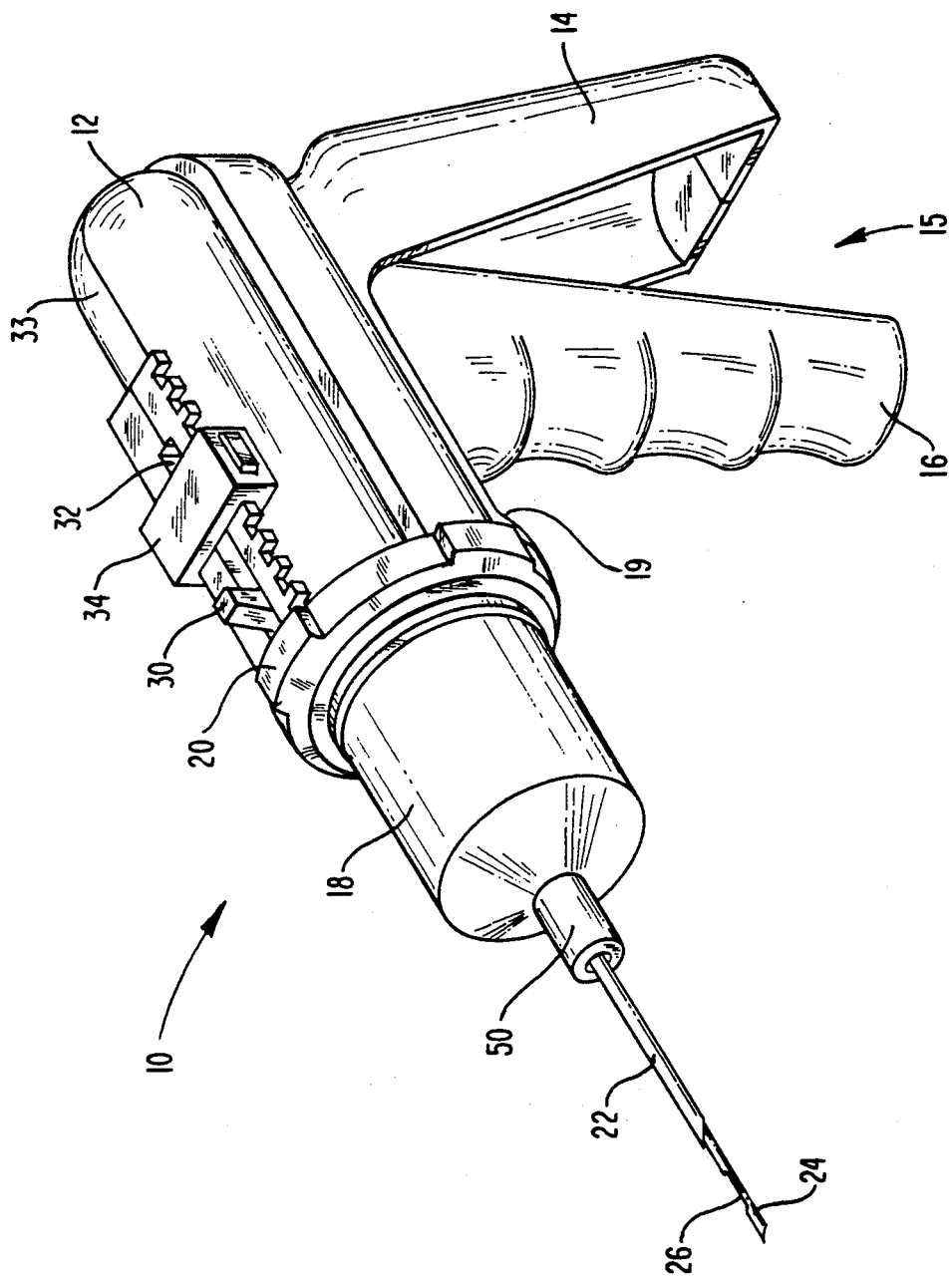
FIG. 1 is an overall perspective view of a preferred embodiment of a pistol-grip soft tissue biopsy device constructed and operated in accordance with the principles of the present invention.

Referring now to FIG. 1, there is shown an overall perspective view of a preferred embodiment of a pistol-grip soft tissue biopsy device 10, for use in performing biopsy procedures. As discussed herein, biopsy procedures include aspiration of fluids, and the term "tissue" includes tissue and fluid mixtures.

Device 10 comprises a housing 12 shaped with a rear portion 14 of a pistol-grip handle 15, the front portion 16 of which is seated in housing 12 in movable fashion. A disposable syringe unit 18 is removably seated in the front end 19 of housing 12, and is held therein by retaining ring 20. Extending from syringe unit 18 is a cannula 22 within which there is slidably engaged a stylet 24. A depression 26 is formed at the distal end of stylet 24, for receiving a deposit of organ tissue. The sharp tip of cannula 22 and stylet 24 enable skin penetration.

As will be explained further herein, enclosed in housing 12 is a retraction mechanism (FIG. 2), which is operable to retract a piston 28 slidably seated in disposable syringe unit 18. A lever 30 associated with the retraction mechanism projects from a slot 32 formed in the upper side 33 of housing 12, and lever 30 is movable in slot 32 until it contacts a cam 34 adjustably seated over slot 32. Cam 34 thus limits lever 30 motion.

Figure 2:
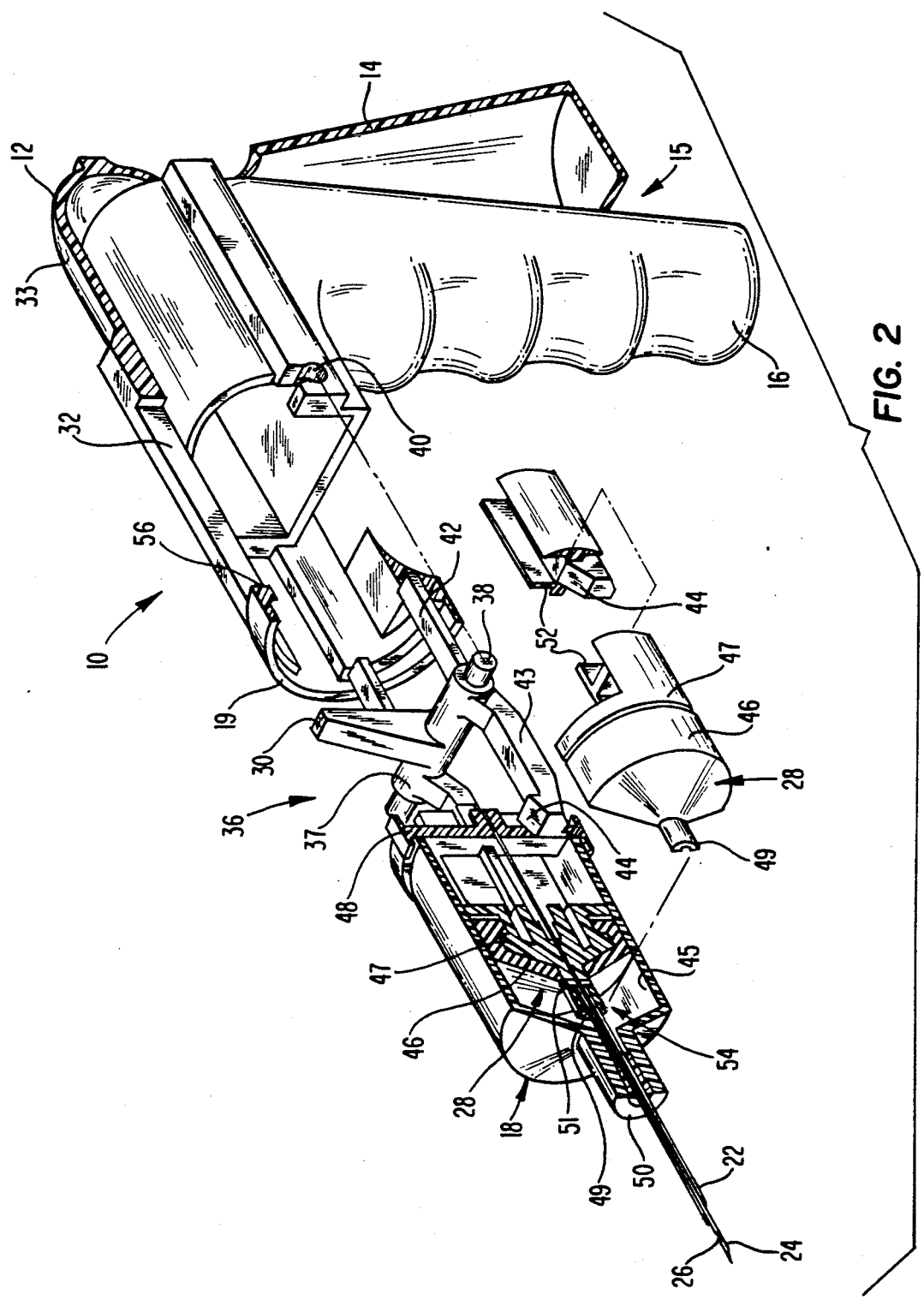
FIG. 2 is an exploded perspective view showing the internal construction of the biopsy device of FIG. 1.

Referring now to FIG. 2, there is illustrated an exploded perspective view showing the internal construction of biopsy device 10, comprising piston 28 and retraction mechanism 36.

Retraction mechanism 36 is constructed as a movable fork mounted 37 on an axle 38, the ends of which are seated in notches 40 formed in handle portion 16. Axle 38 moves rearwardly in housing 12 when pistol-grip handle 15 is squeezed and front handle portion 16 moves against rear handle portion 14. Movable fork 37 has integrally formed therewith a pair of leaf springs 42 which extend into housing 12 to maintain lever 30 upright. A pair of arms 43 with hook ends 44 extend from movable fork 37.

As shown in FIG. 2, piston 28 is slidably seated in the cylindrical interior wall 45 of disposable syringe unit 18. Piston 28 comprises a shaped rubber gasket 46 mounted on a piston body 47, forming a seal against interior wall 45. Stylet 24 is anchored in end clip 48 attached to syringe unit 18, and extends outward through piston body 47 and neck 49 formed therein, and via tip 50 of syringe unit 18. Cannula 22 terminates at one end in neck 49 of piston body 47, and slides over stylet 24 as piston 28 slides in syringe unit 18. An opening 51 (FIG. 3) formed in neck 49 connects the interiors of cannula 22 and syringe unit 18.

For clarity of illustration, the section of piston 28 shown in the foreground in perspective further defines the shape of piston body 47, with a guide member 52 extending rearwardly. The cutaway section of guide member 52 illustrates its engagement with arms 43 via hook ends 44, so that piston 28 moves therewith.

In operation, when cannula 22 penetrates the skin during a biopsy procedure, pistol-grip handle 15 is squeezed so that handle portions 14 and 16 move toward one another. Movable fork 37 is then retracted by rearward movement of notches 40. Retraction of movable fork 37 also retracts piston 28 within syringe unit 18, developing a suction chamber 54 therein. As piston 28 is retracted, cannula 22 is withdrawn, exposing stylet 24 and depression 26 formed therein. Opening 51 connects the suction in suction chamber 54 to cannula 22 and depression 26.

Upon initial retraction of piston 28, the suction causes tissue to enter cannula 22 and become lodged in depression 26. Since the volume ratio of suction chamber 54 to cannula 22 is high, the suction developed at the tip of cannula 22 causes firm seating of tissue in depression 26. This assists in maintaining the tissue compact and unaffected by cannula 22 sliding movement.

With continued retraction of piston 28, lever 30 moves rearwardly in slot 32, until further rearward motion is limited by its contact with cam 34. Lever 30 is forced by cam 34 to rotate counterclockwise, and movable fork 37 also rotates on axle 38. Arms 43 move downward against the tension in leaf springs 42, releasing the engagement of hooks 44 with guide members 52. By vacuum-spring action, piston 28 is shot forward and restored to its position, thrusting cannula 22 forward, to cut the tissue in stylet depression 26, and complete the biopsy procedure.

In accordance with the principles of the present invention, the suction developed in suction chamber 54 serves two functions, by insuring retention of the tissue deposit in stylet depression 26, and providing vacuum-spring action for piston 28. The vacuum-spring provides constant force while piston 28 slides.

When used in aspiration procedures, the pistol-grip handle 15 allows effective control of the suction level, as the fluids which are withdrawn fill cannula 22 and suction chamber 54. The suction assists performance of fine needle aspiration.

Upon removal of the biopsy device 10 from the skin, the pistol-grip handle 15 can be squeezed gently, exposing the stylet depression 26, for removal of the tissue for laboratory analysis. A release valve 55 (FIG. 3) may be provided to prevent suction development in unit 18, allowing easier tissue deposit removal.

The disposable syringe unit 18 can then be removed by first releasing retaining ring 20 and insuring that hooks 44 of arms 43 are released from engagement with guide members 52 of piston 28. End clip 48 which is attached to syringe unit 18 can then be depressed to release it from engagement with an annular shoulder 56 formed in housing 12. A replacement syringe unit 18 is then inserted into the front end 19 of housing 12, clip 48 is engaged with shoulder 56, and retaining ring 20 is replaced.

FIG. 3 shows a partial detail view of the section of biopsy device 10 shown in FIG. 2, featuring a release valve 55. Valve 55 may be provided as a slidable rubber seal mounted on tip 50 of unit 18, for opening aperture 53 to the atmosphere, to avoid the development of suction. Further details of syringe unit 18 construction are revealed, including conical plugs 57 and 58, which retain, respectively, seals 59 and 60 in place, to prevent air leakage into suction chamber 54. Opening 51 is also shown, allowing communication between suction chamber 54 and cannula 22.

Also shown in FIG. 3 is the structure of stylet 24, in which two steps are formed, depression 26 at the stylet 24 end, and a long, shallow depression 62 extending the stylet 24 length. Depression 62 connects suction chamber 54 with the cannula 22 tip.

FIG. 4 shows a partial detail view featuring the shape with which the tips of stylet 24 and cannula 22 are formed. The acute angle formed on the upper edge of cannula 22 is smaller than that formed on the upper edge of stylet 24, to insure efficient cutting of more tissue as cannula 22 slides over stylet 24.

The invention biopsy device 10 can be constructed from plastic and rubber materials, to achieve lower production costs in a mechanically simple, reliable design. The pistol-grip handle may be a re-usable plastic design, and due to its low cost, may also be provided as a disposable design, as required by the user.

Having described the invention with regard to certain specific embodiments thereof, it is to be understood that the description is not meant as a limitation, since further modifications may now suggest themselves to those skilled in the art, and it is intended to cover such modifications as fall within the scope of the appended claims.

We claim:

1. A soft tissue biopsy device comprising:
   a cylindrical housing having a piston being slidably retractable therein, said piston having a cannula extending distally therefrom and being in communication with said housing, said piston being slidably seated on a stylet fixed at one to said housing, said stylet being slidably engaged along its length in said cannula such that its distal end protrudes therefrom;
   means for retracting said piston from an initial position within said housing, to withdraw said cannula and expose said stylet distal end, while developing a suction chamber within said housing and along said cannula length; and
   a cam for limiting retraction of said piston by releasing said piston retraction means, to restore said piston to its initial position within said housing by vacuum-spring action of said suction chamber, such that when the device is inserted into organ tissue to perform a biopsy procedure, retraction of said piston develops said suction chamber in said housing and along said cannula length to draw a portion of said tissue into a depression formed on said stylet distal end, whereupon said cam releases said piston which is shot forward in said housing, and said cannula slides over said stylet to cut and retain said tissue portion in said depression.

2. The biospy device of claim 1 wherein said cylindrical housing is seated within a pistol-grip housing and said retraction means comprises a fork arranged for sliding motion within said pistol-grip housing by squeezing a handle extending therefrom, said fork engaging said piston and retracting it, a lever extending from said fork contacting said cam, causing it to rotate and release said fork and piston engagement.

3. The biopsy device of claim 2 wherein said cam is adjustable to release said fork and piston engagement as desired.

4. The biopsy device of claim 2 wherein said cylindrical housing, piston, cannula and stylet are provided as a replaceable unit, which engages said pistol-grip housing.

5. The biopsy device of claim 2 wherein said pistol-grip handle is designed for single-handed retraction means operation.

6. The biopsy device of claim 2 wherein said pistol-grip handle enables control of fluid sampling in aspiration procedures.

7. The biopsy device of claim 1 wherein the suction volume in said suction chamber is predetermined by adjustment of said cam.

8. The biopsy device of claim 1 wherein said vacuum-spring action provides constant force as said piston is shot forward.

9. The biopsy device of claim 1 wherein said cylindrical housing has a volume significantly greater than that of said cannula, to develop a high suction level in said cannula length with initial piston retraction and securely retain organ tissue.

10. The biopsy device of claim 1 wherein said vacuum-spring action insures quick cutting of tissue.

11. The biopsy device of claim 1 wherein said cannula tip has an upper edge formed with an acute angle smaller than that of said stylet tip, to insure efficient cutting of an increased quantity of tissue.

12. A method of performing soft tissue biopsy comprising the steps of:
   providing a cylindrical housing having a piston being slidably retractable therein, said piston having a cannula extending distally therefrom and being in communication with said housing, said piston being slidably seated on a stylet fixed at one end to said housing, said stylet being slidably engaged along its length in said cannula such that its distal end protrudes therefrom;
   retracting said piston from an initial position within said housing, to withdraw said cannula and expose said stylet distal end, while developing a suction chamber within said housing and along said cannula length; and
   limiting retraction of said piston by release thereof, to restore its initial position within said housing by vacuum-spring action of said suction chamber,
   such that when the device is inserted into organ tissue to perform a biopsy procedure, retraction of said piston develops said suction chamber in said housing and along said cannula length to draw a portion of said tissue into a depression formed on said stylet distal end,
   whereupon limitation of said piston retraction causes it to be released and shot forward in said housing, and said cannula slides over said stylet to cut and retain said tissue portion in said depression.

13. The method of claim 12 wherein said cylindrical housing is seated within a pistol-grip housing and said piston is retracted by a fork arranged for sliding motion within said pistol-grip housing by squeezing a handle extending therefrom, said fork engaging said piston, a lever extending from said fork limiting said piston retraction by releasing said engaged fork and piston.

14. The method of claim 13 wherein said handle enables control of fluid sampling in aspiration procedures.

15. The method of claim 13 wherein said handle enables single-handed piston retraction operation.

16. The method of claim 12 wherein said piston retraction limitation is predetermined in adjustable fashion.

17. The method of claim 12 wherein the suction volume of said housing suction is predetermined in adjustable fashion.

18. The method of claim 12 wherein said cylindrical housing has a volume significantly greater than that of said cannula, to develop a high suction level in said cannula length with initial piston retraction, and securely retain organ tissue.

19. The method of claim 12 wherein said vacuum-spring action insures quick cutting of tissue.

20. The method of claim 12 wherein said vacuum-spring action provides constant force as said piston is shot forward.

* * * * *